United States Patent [19]

Koga et al.

[11] Patent Number: 4,645,341
[45] Date of Patent: Feb. 24, 1987

[54] DOUBLE POLARIZED LIGHT BEAM SPECTROPHOTOMETER OF LIGHT SOURCE MODULATION TYPE

[75] Inventors: Masataka Koga, Katsuta; Masatoshi Kitagawa; Konosuke Oishi, both of Mito, all of Japan

[73] Assignee: Hitachi, Ltd., Tokyo, Japan

[21] Appl. No.: 604,939

[22] Filed: Apr. 27, 1984

[30] Foreign Application Priority Data

Apr. 28, 1983 [JP] Japan .................................. 58-73923

[51] Int. Cl.<sup>4</sup> .......................... G01J 3/42; G01N 21/74
[52] U.S. Cl. ..................................... 356/307; 356/312; 356/323
[58] Field of Search ............... 356/307, 311, 312, 315, 356/319, 320, 323, 325

[56] References Cited

U.S. PATENT DOCUMENTS

| | | | |
|---|---|---|---|
| 3,676,004 | 7/1972 | Prugger et al. | 356/320 |
| 4,165,937 | 8/1979 | Murayama et al. | 356/312 |
| 4,340,307 | 7/1982 | Diamond et al. | 356/320 |
| 4,341,470 | 7/1982 | Parker et al. | 356/307 |
| 4,377,342 | 3/1983 | Koizumi et al. | 356/307 |

FOREIGN PATENT DOCUMENTS

0036788  3/1979  Japan .................................. 356/307

OTHER PUBLICATIONS

Stephens, *Talanta*, vol. 25, No. 8, pp. 435–440, 1978.
Ito, *Anal. Chem.*, vol. 52, No. 11, pp. 1592–1595, 1980.
Koizumi et al., *Anal. Chem.*, vol. 49, No. 8, pp. 1106–1112, 1977.

*Primary Examiner*—F. L. Evans
*Assistant Examiner*—Joel L. Harringa
*Attorney, Agent, or Firm*—Antonelli, Terry & Wands

[57] ABSTRACT

A double polarized light beam spectrophotometer of a light-source modulation type. A modulated light beam emitted by a light source is conducted through specimen atom vapor generated by a graphite atomizer. Wavelength of light undergone atom absorption is selected and spatially separated into a pair of linearly polarized light beams perpendicular to each other. The pair of the linearly polarized light beams separated are alternately passed through a chopper and received by a photoelectric conversion device to be converted into electric signals which are utilized for determining atomic absorption of the specimen. The phase of modulation of light radiated from the light source is synchronized with phase of a current supplied to the graphite atomizer for heating thereof and the switching timing of the chopper.

16 Claims, 10 Drawing Figures

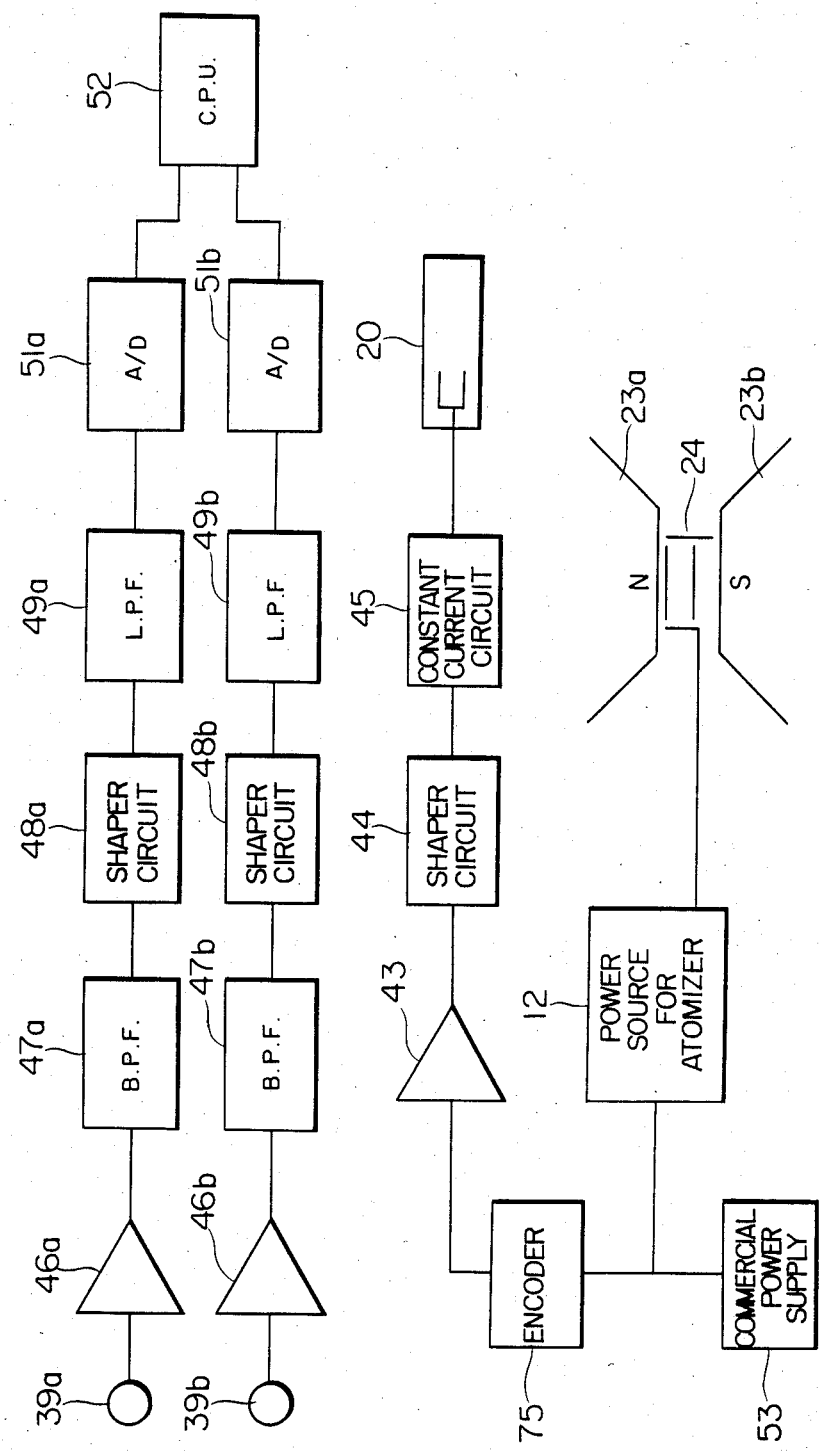

DOUBLE POLARIZED LIGHT BEAM SPECTROPHOTOMETER OF LIGHT SOURCE MODULATION TYPE

BACKGROUND OF THE INVENTION

The present invention generally relates to a double polarized light beam spectrophotometer of a light-source modulation type and in particular to a double polarized light beam spectrophotometer of the light-source modulation type which is advantageously suited for use in Zeeman atomic absorption type photometry.

In the spectrophotometer, it is known to produce a modulated light beam produced by a light source by correspondingly modulating electric power supplied to the light source for excitation thereof. The use of the modulated light thus produced is certainly effective for eliminating noise components generated in a specimen chamber or the like.

In the accompanying drawings, FIG. 1 is a view for graphically illustrating comparatively a relationship between a modulating frequency and a noise frequency. The optical noise 2 produced in the specimen chamber or the like is predominant in a relatively low frequency region. In contrast, the modulating frequency ($f_O$) of the light source is selected at a relatively high value, as indicated by a line 1. Accordingly, even when the noise frequency and the modulating frequency coexist optically, the modulating frequency component 1 of the light source can be easily discriminated from the noise 2 generated in the specimen chamber or the like after both the frequencies have been converted into electric signals. For example, a major part of the noise components 2 generated in the specimen chamber can be eliminated by using a band-pass filter having a center frequency corresponding to the modulating frequency $f_O$ or by using a high-pass filter for passing therethrough the frequency components higher than the frequency $f_O$, whereby a satisfactory S/N ratio can be realized. However, it has been found that the double polarized light beam spectrophotometer of the light-source modulation type with which the present invention is concerned can not assure operation with a satisfactorily high accuracy merely by resorting to the use of the filters of the type mentioned above.

For example, in the double polarized light beam spectrophotometer of the light-source modulation type in which the Zeeman effect is made use of, the modulated light radiated by the light source undergoes Zeeman atomic absorption by specimen vapor and is subsequently subjected to selection of wavelength through a monochromator. Thereafter, the light of the selected wavelength is spatially separated into a polarized light component termed the sample light which is in parallel with the magnetic field and a polarized light component referred to as the reference light which is perpendicular to the magnetic field. The sample light beam and the reference light beam pass alternately through a rotary chopper to be received by a common photomultiplier tube. The signal resulting from the photoelectric conversion is of such waveform as shown in FIG. 2 in which time is taken along the abscissa with the current intensity being taken along the ordinate. The modulation of the light source is illustrated by vertical lines, wherein the maximum light emission is indicated by the vertical lines among which the minimum light levels intervene. High and low levels in magnitude of the arrayed vertical lines are explained by the fact that the sample light indicated by 4 and the reference light indicated by 3 and 5 are alternately changed over in a double beam optical system. It is assumed that the switching frequency at which the sample and the reference light are changed over is 50 Hz (i.e. the number of the switching times is 100 per second) and that the modulating frequency of the light source is 1483.33 Hz. That is, the ratio of the switching frequency of the chopper to the modulating frequency is at the ratio of 3 to 89. So long as this ratio is accurately maintained, there exists deviation of ⅓ of the modulation period of the light source between the preceding reference light 3 and the succeeding reference light 5, as a result of which the phase of the reference light coincides with the phase of the modulated light every third period, giving rise to generation of a beat signal having a frequency of 16.7 Hz which corresponds to ⅓ of the switching frequency of 50 Hz.

Besides, since the ratio 3:89 of the two frequencies mentioned above will not be perfectly stabilized but will fluctuate slightly, a beat signal of another frequency may often be produced. For example, when the ratio of 3 to 89.1 is slightly varied to 3 to 39.1 which is equivalent to 10:297, there is produced a beat signal of 5 Hz which is 1/10 of the switching frequency. In this way, when the modulation of the light source and the switching or changing-over between the sample light and the reference light are controlled independent of each other, there is inevitably produced a beat signal having a frequency which is necessarily subjected to variations. Thus, great difficulty is encountered in eliminating this type of beat signal.

Next, examination will be made as to the magnitude of the amplitude at which the beat components make an appearance in the detected output signal. Referring to FIGS. 3A and 3B which correspond to the view shown in FIG. 2 and enlarged along the abscissa, there is illustrated how much of the light quantity can be received by a photomultiplier tube during an interval of 10 m sec (because of 100 switchings per second) of the sample light or reference light. It is assumed that the light source is sinusoidally modulated and that the frequency component of 14.833... of the light source is received, although the overall light amount as received depends on the position of the modulated light source. FIG. 3A shows the case where the light quantity or amount received by the photomultiplier tube is at a maximum, while FIG. 3B shows the case where the received light amount is at a minimum. In these figures, components 6 and 7 of 14 periods are shown discriminatively from the components 8 and 9 of 0.833 period. The component of 0.833 period illustrated in FIG. 3A covers an area of 0.993 while the periodic component 9 of 0.833 period shown in FIG. 3B covers an area of 0.674.

However, since the area for one period is standardized to 1 (unit), the ratio of area occupied by the two components mentioned above is 14.674 to 14.993. Accordingly, when the light absorption in the case illustrated in FIG. 3A is assumed to be zero, the light absorption in the case illustrated in FIG. 3B corresponds to 0.009.

In the foregoing, the frequency of the beat generated in the hitherto known spectrophotometer has been examined in conjunction with FIG. 2, while examination has been made by referring to FIGS. 3A and 3B as to the possibility of the beat having an amplitude corresponding to the light absorption of 0.009. In this way, generation of the beat is inevitable in the prior art spectrophotometry, involving a large burden on the signal processing for reducing such beat signals while notwithstanding rendering it very difficult to attain a satisfactory accuracy or precession in the displayed value of measurement, to a serious disadvantage.

In case a graphite atomizer is used for atomization or vaporization of the specimen, a commercial frequency current of 400 A at maximum is supplied to the atomizer. As a consequence, the atom vapor generated in the atomizer undergoes fluctuation at the commercial line frequency, bringing about a variation in frequency in the Zeeman atomic absorption. Since this frequency variation will correspond to the switching frequency of the chopper described hereinbefore, beat signals will also be produced due to the phenomena discussed above in conjunction with FIGS. 2, 3A and 3B.

SUMMARY OF THE INVENTION

An object of the present invention is to overcome the difficulties of the hitherto known spectrophotometers described above and provide a double polarized light beam spectrophotometer of light source modulation type which is capable of fundamentally suppressing the generation of the beats.

In view of the above object, it is proposed according to a feature of the invention that, with respect to the frequency of the light source modulating signal, the frequency of the current supplied to the graphite atomizer and the switching frequency of the light chopper at least two of these frequencies are mutually locked or synchronized at a ratio corresponding to an integer.

BRIEF DESCRIPTION OF THE DRAWINGS

FIG. 9 is a circuit diagram showing an electrical system employed in the system shown in FIG. 8.

DESCRIPTION OF THE PREFERRED EMBODIMENTS

Figure 4:
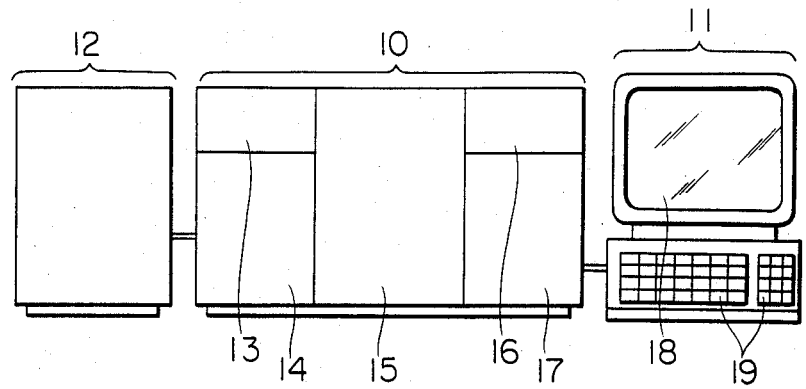
FIG. 4 is an external pictorial view showing schematically a double polarized light beam spectrophotometer according to an embodiment of the invention.

FIG. 4 is a schematic pictorial view showing a double polarized light beam spectrophotometer of light-source modulation type in which the Zeeman effect is made use of according to an embodiment of the present invention. The spectrophotometer system is essentially constituted by three units, i.e. a photometer unit 10, a data processing unit 11 and a power source unit 12 for a graphite atomizer. The photometer unit 10 is composed of a hollow-cathode lamp chamber 13, a gas control apparatus 14, a graphite atomizer 15, a spectroscope controller 16 and an electric circuit unit 17. The data processing unit 11 includes a CRT display 18 and a keyboard 19. The data processing unit may further be provided with a plotter, a recorder, a floppy disc unit, an interface device for communication with an external computer and the like.

Figure 5:
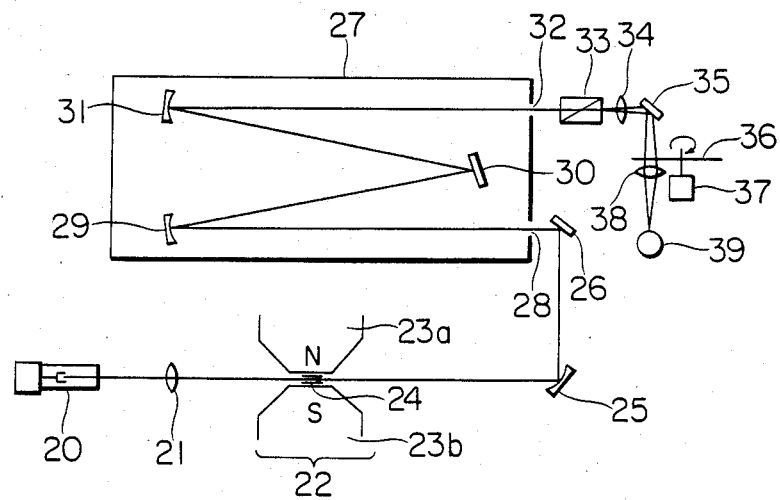
FIG. 5 is a view showing schematically an optical system employed in the apparatus shown in FIG. 4.

FIG. 5 shows an optical system which may be used in the spectrophometer system shown in FIG. 4. Referring to FIG. 5, light emitted by a hollow-cathode lamp or electrodeless discharge tube 20 is focussed by a lens 21 to a specimen atom vapor generator 24 of a Zeeman graphite atomizer 22. The light beam having passed through the specimen atom vapor generator 24 is reflected by a mirror 25 and directed to a mirror 26 in the focussed state. The light beam reflected by the mirror 26 impinges on an entrance slit 28 of the spectroscope 27. The Zeeman graphite atomizer 22 comprises a cylindrical electrode of graphite in which the specimen atom vapor generator 24 capable of transmitting light is disposed and a pair of magnets 23a and 23b between which the cylindrical graphite electrode is positioned. Among the light rays of particular wavelengths subjected to the Zeeman atomic absorption, the polarized light component parallel to the magnetic field is absorbed by the specimen atoms while the polarized light component perpendicular to the magnetic field undergoes absorption by the specimen atoms only a little. On the other hand, a background component is produced by molecules and other particles. In other words, the two types of the polarized light components mentioned above are absorbed by molecules and other particles to the same degree, to produce the background component, which can however be cancelled by subtracting the two polarized light components from each other, whereby only the light component representative of the atomic absorption is obtained. The light beam which has undergone the atomic absorption is selected by the spectroscope 27 to be emitted from an exit slit 32 after having been reflected and diffracted by collimating mirrors 29 and 31 and a plane diffraction grating 30.

The light beam having the exit slit 32 is spatially separated into a sample light beam (the polarized light component parallel to the magnetic field) and a reference light beam (polarized light component perpendicular to the magnetic field) by means of a polarizing prism 33 which may be constituted by a Wollaston prism. The image appearing at the exit slit 32 is focussed on a chopper 36 by way of a lens 34 and a mirror 35. As will be seen, the two polarized light components follow the same path in the optical system to be finally separated spatially. In this sense, the illustrated photometry system may be referred to as a double polarized light beam spectrophotometer system. The chopper 36 is so constructed as to pass there-through either one of the sample light or the reference light at one time.

Figure 7:
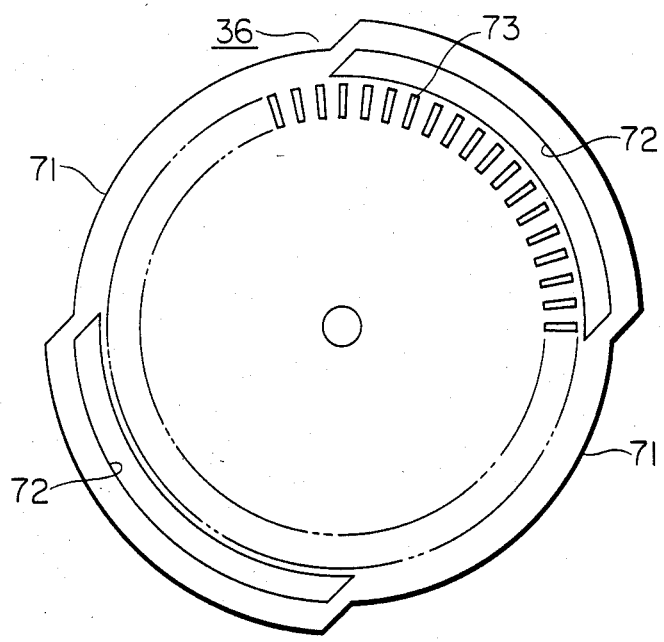
FIG. 7 is a top plan view showing a structure of a disc-like chopper.

A typical structure of the chopper 36 is shown in FIG. 7. More specifically, the chopper 36 is constituted by a disc having recesses 71 formed in the outer periphery for passing the sample light and arcuate slots 72 formed in the disc along the peripheral edge portion destined for passing the reference light. The sample light and the reference light separately gated through the chopper 36 are again focussed through a lens 38 to impinge alternately on the same location at which is positioned the light receiving face of a photomultiplier tube 39 for detection. In other words, images making appearance at a light beam splitting point of the Wollaston prism 33 are focused on the light receiving plate of the photomultiplier tube 39. By the way, the chopper 36 is rotated at a constant speed by a synchronous motor 37.

Figure 6:
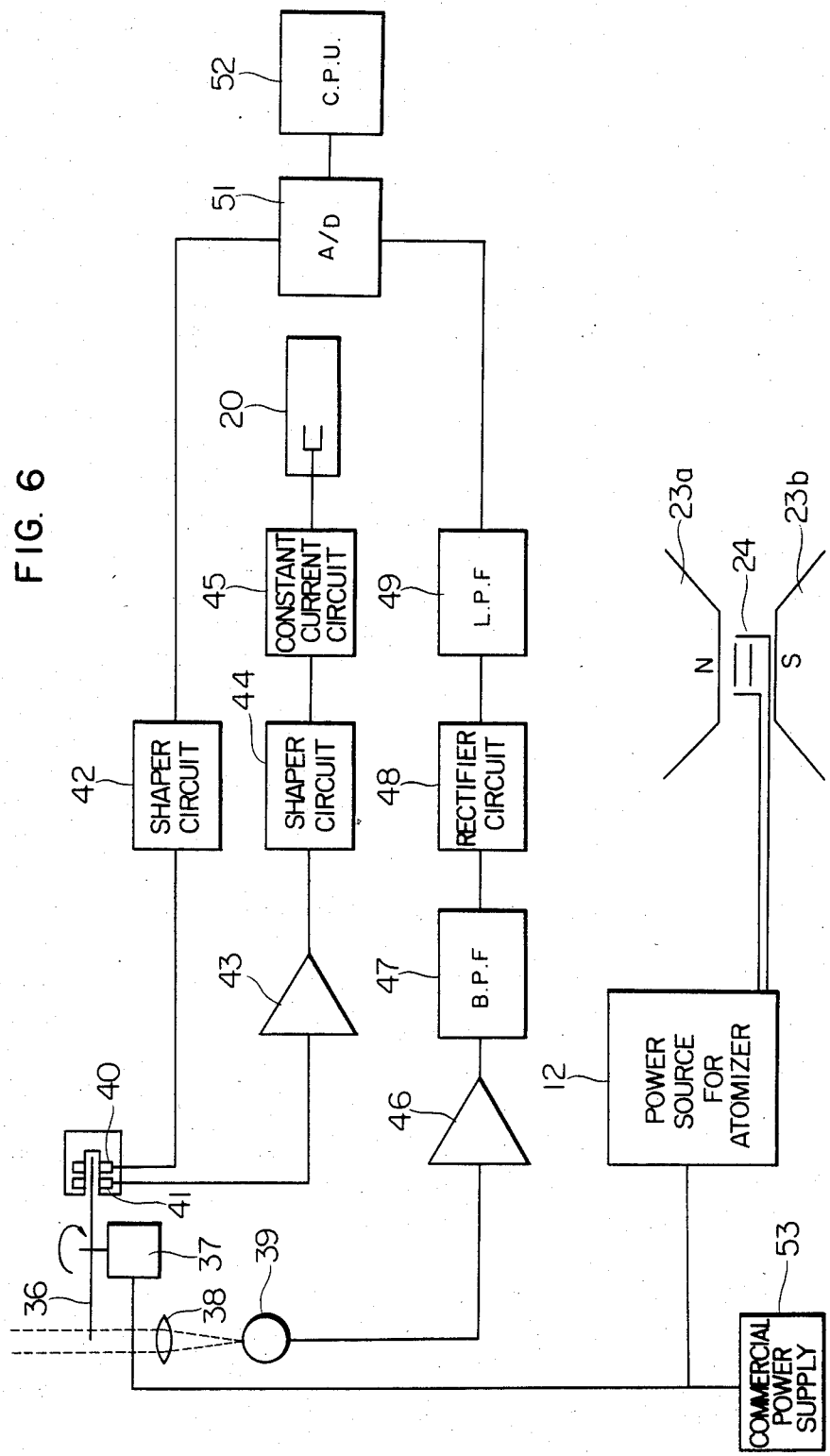
FIG. 6 shows a circuit diagram of an electrical system employed in the system shown in FIG. 4.

FIG. 6 shows in a circuit diagram an electrical circuit used in the photometric system shown in FIG. 5. In FIG. 6, like parts as those shown in FIG. 5 are denoted by the same reference numerals. During the constant rotation of the chopper 36, the sample light and the reference light are alternately detected by the photomultiplier tube 39. To this end, a pair of photocoupler arrays 40 and 41 are disposed along the peripheral edge portion of the chopper disc 36 at respective positions diametrically opposite to that at which the light beams to be detected are transmitted through the chopper 36. More particularly, the photocoupler 40 is so constructed as to detect the time when the light passes through the slot 72, to thereby produce a detection signal for discriminatively identifying the reference light and the sample light from each other. The output signal of the photocoupler 40 is supplied to an analogue-to-digital or A/D converter 51 by way of a waveform shaper circuit 42.

On the other hand, the photocoupler 41 is so arranged as to detect the passage of the light beam through the rectangular slots 73 of the chopper 36. The detection signal outputted by the photocoupler 41 is amplified by a preamplifier 43 and supplied to a constant current circuit 45 by way of a shaper circuit 44. The synchronous motor 37 is rotated at a speed of 1500 r.p.m.. The slots 73 of the chopper amount to 60 in number. Accordingly, the detection signal produced by the photocoupler 41 is at the pulse rate of 1500 Hz. In the constant current circuit 45, the pulse signal having the frequency of 1500 Hz is superposed on a DC (direct current) component, the average current thereof being converted into a constant current. The hollow-cathode lamp 20 is lit by the modulated signal supplied from the constant current circuit 45 to thereby produce a modulated light beam which in turn is converted into an electric signal by the photomultiplier tube 39 after following the optical path as described above in conjunction with FIG. 5. The electric signal output from the photomultiplier tube 39 is amplified by a preamplifier 46 and passes through a band-pass filter 47 where only the modulation frequency component originating in the hollow-cathode lamp 20 is gated through to be supplied to a rectifier circuit 48, a low-pass filter 49 and hence to the A/D converter 51 to undergo A/D conversion in accordance with the timing signal generated on the basis of the output signal of the shaper circuit 42. The digital output signal of the A/D converter 51 is supplied to the central processing unit or CPU 52 where the measured value is obtained after the correction or compensation of the background component on the basis of the sample signal and the reference signal.

Figure 1:
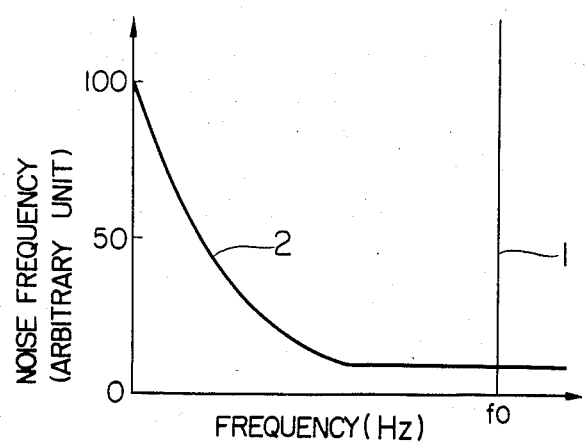
FIG. 1 is a view for graphically illustrating comparatively a relationship between a signal frequency and a noise frequency.
Figure 2:
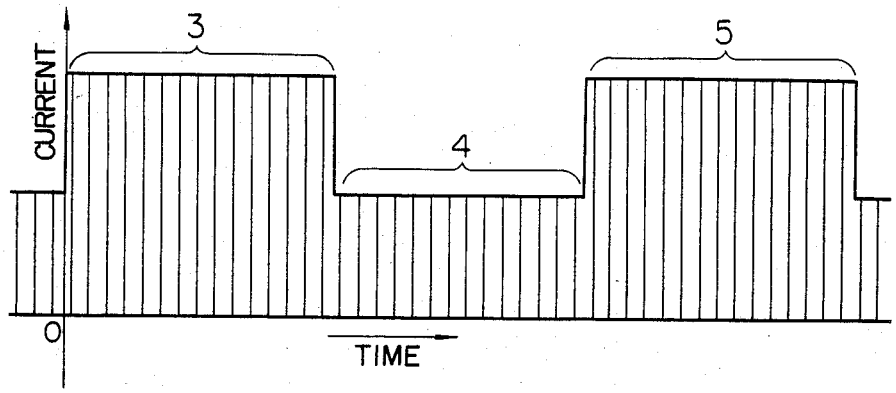
FIG. 2 shows a signal waveform diagram for illustrating a case in which modulation of a light source is out of synchronism with changing-over or switching between a sample light beam and a reference light beam.
Figure 3A:
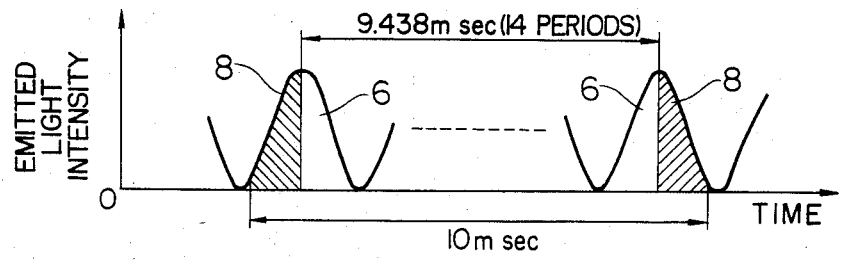
FIGS. 3A and 3B are graphical views for illustrating amplitudes of beat signals.
Figure 3B:
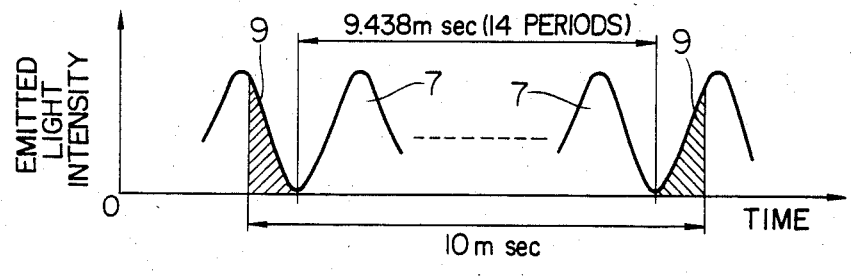

The chopper 36 is rotated by the synchronous motor 37 driven by a power source 53 of a commercial frequency. In other words, the chopper 36 rotates in synchronism with the commercial line frequency. Further, the light emitted by the hollow-cathode lamp 20 is modulated in accordance with the signal representative of the light passing through the slots 73 of the chopper 36. In this connection, the reference light and the sample light are alternately switched by means of the recesses 71 and the arcuate slots 72. Accordingly, the switching timing of the chopper is constantly in synchronism with a predetermined phase position of the light modulation signal. Thus, there arises no problem mentioned above by referring to FIGS. 3A and 3B at all.

Furthermore, since the power source 12 for the graphite atomizer is driven at the same frequency as the commercial line frequency while the chopper 36 is rotated by the synchronous motor 37 driven by the power source 53, fluctuation in the atom vapor generated in the graphite atomizer occurs in synchronism with the commercial line frequency. Accordingly, no periodic variations or fluctuations occur in the detected or measured value.

As will be understood from the above description of the illustrated embodiment, the switching or changing-over between the sample light and the reference light, modulation of the hollow-cathode lamp and the heating of the specimen atom vapor generator 24 are carried out constantly in synchronism with one another on the basis of a common frequency corresponding to that of the power supply source. Accordingly, no beat is produced. Thus, there can be obtained data of measurement with a significantly improved S/N ratio to assure a remarkably increased measurement accuracy.

In the foregoing description, it has been assumed that the graphite atomizer is employed as the specimen vapor generator. When flame light is used to this end, the power source 12 for the graphite atomizer can of course be spared. In this case, the desired object can be accomplished by changing over the sample light with the reference light in synchronism with the modulation of the light source. In that case, the motor 37 obviously need not be driven in synchronism with the commercial frequency. A pulse motor may be used in place of the synchronous motor.

Figure 8:
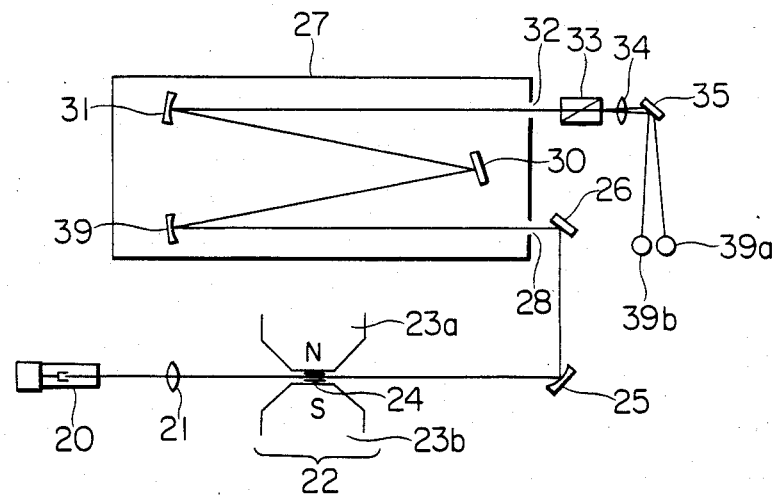
FIG. 8 is a view showing an optical system for the spectrophotometer according to another embodiment of the invention.

Another embodiment of the invention is shown in FIG. 8 in which elements or parts corresponding to those shown in FIG. 5 are denoted by like reference symbols. The embodiment shown in FIG. 8 differs from the one shown in FIG. 5 in respect that no chopper is provided and that two polarized light components are received by a pair of photomultiplier tubes 39a and 39b, respectively. In this case, it is required that the two photomultiplier tubes exhibit substantially identical characteristics.

FIG. 9 shows an electrical circuit system used in the embodiment shown in FIG. 8. The electric signals detected by the photomultiplier tubes 39a and 39b, respectively, are processed through the band-pass filters 47a and 47b, the shaper circuits 48a and 48b, low-pass filters 49a and 49b to be supplied to the A/D converters 51a and 51b for undergoing A/D conversion, respectively. The CPU 52 fetches the sample signal and the reference signal from the A/D converters 51a and 51b at an appropriate timing to determine the light absorption through subtraction of both the reference and the sample light signals. The specimen atom vapor generator 24 is constituted by a graphite atomizer and supplied with a current from a power supply source 12 which is driven at the same frequency as the commercial line frequency. On the other hand, an encoder 75 includes a synchronous motor and a chopper as in the case of the embodiment shown in FIG. 6. However, the chopper differs in structure from the one shown in FIG. 7. More particularly, although the chopper has sixty slots 73, neither the recesses 71 nor the arcuate slots 72 are provided. The encoder produces a pulse signal having a frequency of 1500 Hz in synchronism with the frequency of the power supply source 53. This pulse signal is supplied to the hollow-cathode lamp 20 after having been processed through the amplifier 43, the waveform shaper circuit 44 and the constant current circuit 45 in the manner similar to the case of the embodiment shown in FIG. 6. Accordingly, the modulation of the hollow-cathode lamp 20 is constantly synchronized with the heating current supplied to the graphite atomizer, producing no undesirable fluctuations or variations in the detection signal due to the beat phenomenon.

As will be appreciated from the foregoing description, synchronization among a plurality of frequency signals is performed at the stage of generation of these signals according to the teachings of the invention, whereby generation of the beat is positively suppressed with the S/N ratio being significantly improved, assuring thus high effective and economical signal processing.

We claim:

1. A double polarized light beam spectrophotometer system of a light-source modulation type operated from a power supply source, comprising:
   means for modulating light emitted by a light source;
   atomizing means positioned to receive said modulated light for generating an atom vapor of a specimen and for causing said modulated light to undergo atomic absorption of polarized light components of the modulated light as it passes through the atom vapor;
   optical means for selecting a wavelength of the light which has undergone atomic absorption in said atomizing means and for spatially separating the light of the selected wavelength into a pair of linearly polarized light beams;
   extracting means for alternately extracting said pair of the linearly polarized light beams separated by said optical means;
   photoelectric conversion means for receiving said pair of the linearly polarized light beams alternately extracted by said extracting means;
   signal means for providing signals at the modulation frequency corresponding to said pair of the linearly polarized light beams detected by said photoelectric conversion means;
   means for determining the light absorption of said specimen on the basis of the signals from said signal means; and
   synchronizing means for generating at least one synchronous signal in phase synchronism with the alternate extracting operation of said extracting means, said light modulating means including means for modulating the light on the basis of said synchronous signal and said signal means including means for applying said signals to said determining means on the basis of said synchronous signal.

2. A double polarized light beam spectrophotometer system according to claim 1, wherein said extracting means is composed of a chopper device.

3. A double polarized light beam spectrophotometer system according to claim 2, wherein said chopper device includes a disc-like chopper having light transmitting portions and light interrupting portions for extracting alternately said pair of the linearly polarized light beams, and drive means for driving said chopper.

4. A double polarized light beam spectrophotometer system according to claim 3, wherein said synchronizing means includes a plurality of slots formed equidistantly in said chopper along a circumferential direction, and photocoupler means having an optical path located at a position which said plurality of the slots intercept, said light modulating means performing the light modulation on the basis of the signal produced by said photocoupler means.

5. A double polarized light beam spectrophotometer system according to claim 3, wherein said drive means is composed of a motor rotated in synchronism with the frequency of said power supply source.

6. A double polarized light beam spectrophotometer system according to claim 5, wherein said motor is composed of a synchronous motor.

7. A double polarized light beam spectrophotometer system according to claim 1, wherein said atomizing means includes a pair of magnets for producing the Zeeman effect.

8. A double polarized light beam spectrophotometer system according to claim 1, wherein said optical means includes a spectroscope for selecting the wavelength of the light which has undergone atomic absorption and a polarizing prism for spatially separating the light of the selected wavelength into the pair of linearly polarized light beams.

9. A double polarized light beam spectrophotometer system according to claim 8, wherein said polarizing prism is constituted by a Wollaston prism.

10. A double polarized light beam spectrophotometer system according to claim 1, wherein said photoelectric conversion means includes a photoelectric converter and means for focussing said pair of linearly polarized light beams from said extraction means to a light receiving part of said photoelectric converter.

11. A double polarized light beam spectrophotometer system of a light-source modulation type operated from a power supply source, comprising:
   means for modulating light emitted by a light source;
   atomizing means positioned to receive said modulated light for generating an atom vapor of a specimen and for causing said modulated light to undergo atomic absorption of polarized light components of the modulated light as it passes through the atom vapor;
   optical means for selecting a wavelength of the light which has undergone atomic absorption in said atomizing means and for spatially separating the light of the selected wavelength into a pair of linearly polarized light beams;
   extracting means for alternately extracting said pair of the linearly polarized light beams separated by said optical means;
   photoelectric conversion means for receiving said pair of the linearly polarized light beams alternately extracted by said extracting means and for providing signals corresponding to said pair of linearly polarized light beams;
   means for determining the light absorption of said specimen on the basis of the signals corresponding to said pair of the linearly polarized light beams detected by said photoelectric conversion means; and
   synchronizing means for synchronizing at least the switching of said alternate extraction means with the phase of modulation of said light modulating means, wherein said extracting means is composed of a chopper device which includes a disc-like chopper having light transmitting portions and light interrupting portions for extracting alternately said pair of the linearly polarized light beams, and drive means for driving said chopper composed of a motor rotated in synchronism with a frequency of said power supply source, and wherein said atomizing means is constituted by an atomizer heated by a current having the same frequency as that of the output of said power supply source for driving said motor.

12. A double polarized light beam spectrophotometer system according to claim 11, wherein said atomizer is constituted by a graphite atomizer.

13. A double polarized light beam spectrophotometer system of a light-source modulation type operated from a power supply source, comprising:

light modulating means for modulating light emitted by a light source;

atomizer means positioned to receive said modulated light and driven by electric heating means for producing an atom vapor of a specimen and for causing said modulated light to undergo atomic absorption of polarized light components of the modulated light as it passes through the atom vapor;

optical means for selecting a wavelength of the light which has undergone said atomic absorption and for spatially separating the light of the selected wavelength into a pair of linearly polarized light beams;

a pair of photoelectric conversion means for receiving, respectively, said pair of the linearly polarized light beams separated by said optical means;

means for determining light absorption of said specimen on the basis of signals corresponding to said pair of the linearly polarized light beam detected by said photoelectric conversion means; and synchronizing means for synchronizing the phase of modulation of said light modulating means with the phase of a driving current which is supplied to said atomizer means.

14. A double polarized light beam spectrophotometer system according to claim 13, wherein said synchronizing means includes synchronous signal generating means for generating a signal synchronized with the phase of the output of a power supply source for supplying power to said electric heating means, said light modulating means performing the modulation of light on the basis of said synchronized signal.

15. A double polarized light beam spectrophotometer system according to claim 14, wherein said synchronous signal generating means includes an encoder.

16. A double polarized light beam spectrophotometer system according to claim 13, wherein said atomizer is constituted by a graphite atomizer means.

* * * * *